(12) United States Patent
Geric

(10) Patent No.: US 12,246,122 B2
(45) Date of Patent: Mar. 11, 2025

(54) HEART-LUNG MACHINE WITH SEMI-AUTONOMOUS INITIATION MODE

(71) Applicant: Terumo Cardiovascular Systems Corporation, Ann Arbor, MI (US)

(72) Inventor: Joseph Geric, Livonia, MI (US)

(73) Assignee: Terumo Cardiovascular Systems Corporation, Ann Arbor, MI (US)

(*) Notice: Subject to any disclaimer, the term of this patent is extended or adjusted under 35 U.S.C. 154(b) by 581 days.

(21) Appl. No.: 17/314,856

(22) Filed: May 7, 2021

(65) Prior Publication Data

US 2022/0355012 A1 Nov. 10, 2022

(51) Int. Cl.
*A61M 1/36* (2006.01)
*G16H 40/63* (2018.01)

(52) U.S. Cl.
CPC ........ *A61M 1/3667* (2014.02); *A61M 1/3624* (2013.01); *A61M 1/3626* (2013.01); *G16H 40/63* (2018.01); A61M 2205/3389 (2013.01); A61M 2205/502 (2013.01)

(58) Field of Classification Search
CPC .............. A61M 1/3667; A61M 1/3624; A61M 1/3626; A61M 1/3632; A61M 1/3664; A61M 1/367; A61M 1/3666; A61M 1/3621; A61M 1/36224; A61M 1/36225; A61M 2205/3389; A61M 2205/50; A61M 2205/43; A61M 2205/44; A61M 2205/505; A61M 2205/18; A61M 2205/502; A61M 60/232; A61M 60/585; A61M 1/1562; A61M 1/302; A61M 1/303; A61M 1/362262; A61M 2205/3393; G16H 40/63; G16H 20/40; G16H 40/60; G01F 25/20
See application file for complete search history.

(56) References Cited

U.S. PATENT DOCUMENTS

| | | | |
|---|---|---|---|
| 3,946,731 A | 3/1976 | Lichtenstein | |
| 4,231,366 A * | 11/1980 | Schael | A61M 1/308 604/6.11 |
| 6,137,416 A | 10/2000 | Meador | |
| 6,164,920 A | 12/2000 | Nazarian et al. | |
| 6,673,314 B1 | 1/2004 | Burbank et al. | |
| 6,783,328 B2 | 8/2004 | Lucke et al. | |
| 8,409,124 B2 | 4/2013 | Steffens et al. | |

(Continued)

FOREIGN PATENT DOCUMENTS

| | | |
|---|---|---|
| EP | 1166806 | 2/2002 |
| EP | 0852505 | 4/2005 |

(Continued)

OTHER PUBLICATIONS

PCT International Search Report and Written Opinion in International Appln. No. PCT/US2022/025512, dated Jul. 19, 2022, 9 pages.

(Continued)

*Primary Examiner* — Catharine L Anderson
*Assistant Examiner* — Quynh Dao Le
(74) *Attorney, Agent, or Firm* — Fish & Richardson P.C.

(57) ABSTRACT

This document describes medical systems that have features for initiating operational settings during a start-up process. For example, this document describes heart-lung machine systems that are programmed and integrated with features that perform semi-autonomous start-up procedures.

16 Claims, 4 Drawing Sheets

(56) References Cited

U.S. PATENT DOCUMENTS

| | | | |
|---|---|---|---|
| 10,183,107 B2* | 1/2019 | Utsugida | A61M 39/28 |
| 2002/0085952 A1 | 7/2002 | Ellingboe et al. | |
| 2006/0089586 A1 | 4/2006 | Kaus et al. | |
| 2008/0221495 A1 | 9/2008 | Steffens et al. | |
| 2010/0160882 A1* | 6/2010 | Lowe | A61F 13/505 |
| | | | 604/361 |
| 2013/0285812 A1* | 10/2013 | Rantala | A61B 5/746 |
| | | | 340/573.1 |
| 2013/0317560 A1* | 11/2013 | Barnes | A61N 1/3925 |
| | | | 607/6 |
| 2014/0074008 A1* | 3/2014 | Fontanazzi | A61M 1/34 |
| | | | 604/5.04 |
| 2014/0099235 A1 | 4/2014 | Ellingboe et al. | |
| 2017/0021080 A1 | 1/2017 | Bonczar et al. | |
| 2017/0102846 A1 | 4/2017 | Ebler et al. | |
| 2017/0209637 A1* | 7/2017 | Schaefer | A61M 1/34 |
| 2017/0224901 A1 | 8/2017 | Niimi et al. | |
| 2017/0296736 A1* | 10/2017 | Golarits | G16H 20/40 |
| 2019/0038825 A1 | 2/2019 | Muller-Spanka et al. | |
| 2019/0255241 A1* | 8/2019 | Gagel | A61M 1/1692 |
| 2020/0164116 A1* | 5/2020 | Gordon | A61M 1/74 |
| 2020/0169275 A1* | 5/2020 | Chahal | H04B 1/005 |
| 2022/0401637 A1* | 12/2022 | Suffritti | A61M 1/1672 |
| 2023/0177149 A1* | 6/2023 | Ballantyne | G06F 21/565 |
| | | | 210/85 |

FOREIGN PATENT DOCUMENTS

| | | | | |
|---|---|---|---|---|
| WO | WO-2015011473 A1 * | 1/2015 | | A61M 1/0281 |
| WO | WO 2020/136652 | 7/2020 | | |
| WO | WO 2021/052553 | 3/2021 | | |

OTHER PUBLICATIONS

International Preliminary Report on Patentability in International Appln. No. PCT/US2022/025512, mailed on Nov. 16, 2023, 7 pages.

Extended European Search Report in European Appln No. 22799289.8, dated Sep. 17, 2024, 6 pages.

* cited by examiner

HEART-LUNG MACHINE WITH SEMI-AUTONOMOUS INITIATION MODE

BACKGROUND

1. Technical Field

This document relates to medical systems that have features for initiating operational settings. For example, this document relates to heart-lung machine systems that are programmed and integrated with features that perform semi-autonomous start-up procedures.

2. Background Information

Heart-lung machine ("HLM") systems are used, along with an extracorporeal circuit and a hollow fiber oxygenator, to meet a patient's circulatory and blood gas exchange needs during medical procedures such as cardiopulmonary bypass ("CPB") surgery. Blood from the patient is either gravity drained, or VAVD (vacuum assisted venous drainage) is used, to obtain the required amount of blood flow to maintain sufficient volume in a reservoir of the extracorporeal circuit. A pump, such as a peristaltic pump or a centrifugal pump coupled with a magnetic drive system, is sometimes used in the main line of the extracorporeal circuit in order to pump blood from the reservoir, through the oxygenator, and finally back to the patient. In addition to a HLM per se, heart-lung machine systems can include multiple types of patient monitoring devices that are used in conjunction with the HLM.

SUMMARY

This document describes medical systems that have features for initiating operational settings at the beginning of a medical procedure. For example, this document describes HLM systems that are programmed and integrated with features by which the HLM can perform semi-autonomous start-up procedures.

In one aspect, this disclosure is directed to heart-lung machine system that includes an arterial pump, a reservoir level detector, a user interface, and a central computer system. The central computer system is configured to query the reservoir level detector to determine whether the reservoir level detector is active or inactive, and, in response to determining that the reservoir level detector is inactive, automatically activate the reservoir level detector.

Such a heart-lung machine system may optionally include one or more of the following features. The heart-lung machine system may also include an air detector. The central computer system may also be configured to query the air detector to determine whether the air detector is active or inactive, and, in response to determining that the air detector is inactive, automatically activate the air detector. The heart-lung machine system may also include a fast clamp. The central computer system may also be configured to query the fast clamp to determine whether the fast clamp is active or inactive, and, in response to determining that the fast clamp is inactive, automatically activate the fast clamp by closing the fast clamp. The heart-lung machine system may also include a venous occluder. The central computer system may also be configured to query the venous occluder to determine whether the venous occluder is active or inactive, and, in response to determining that the venous occluder is inactive, automatically activate the venous occluder by adjusting the venous occluder to a pre-configured occlusion setting. The arterial pump may be a centrifugal pump. The central computer system may also be configured to query the centrifugal pump to determine whether the centrifugal pump is active or inactive, and, in response to determining that the centrifugal pump is inactive, automatically activate the centrifugal pump by adjusting the centrifugal pump to a pre-configured RPM setting. The central computer system may be configured to stop the adjusting the centrifugal pump to the pre-configured RPM setting in response to a manual input to the heart-lung machine system that effects the RPM setting of the centrifugal pump. In some embodiments, initially after the reservoir level detector is automatically activated, alarms from the reservoir level detector are suppressed by the central computer system. The central computer system may be configured to no longer suppress the alarms from the reservoir level detector in response to a first detection of fluid by the reservoir level detector.

In another aspect, this disclosure is directed to a method of operating a heart-lung machine system. The method includes querying, by a central computer system of the heart-lung machine system, a reservoir level detector of the heart-lung machine system to determine whether the reservoir level detector is active or inactive. The method also includes in response to determining that the reservoir level detector is inactive, automatically activating, by central computer system of the heart-lung machine system, the reservoir level detector.

Such a method may optionally include one or more of the following features. The method may also include, initially after the reservoir level detector is automatically activated, suppressing, by the central computer system, alarms from the reservoir level detector. The method may also include stopping the suppressing of the alarms from the reservoir level detector in response to a first detection of fluid by the reservoir level detector. The method may also include querying, by the central computer system, a centrifugal pump of the heart-lung machine system to determine whether the centrifugal pump is active or inactive. The method may also include in response to determining that the centrifugal pump is inactive, automatically activating the centrifugal pump by the central computer system. Automatically activating the centrifugal pump may include adjusting, by the central computer system, the centrifugal pump to a pre-configured RPM setting. The method may also include stopping, by the central computer system, the adjusting the centrifugal pump to the pre-configured RPM setting in response to a manual input to the heart-lung machine system that effects the RPM setting of the centrifugal pump. The method may also include querying, by the central computer system, an air detector of the heart-lung machine system to determine whether the air detector is active or inactive. The method may also include in response to determining that the air detector is inactive, automatically activating, by central computer system, the air detector. The method may also include querying, by the central computer system, a fast clamp of the heart-lung machine system to determine whether the fast clamp is active or inactive. The method may also include in response to determining that the fast clamp is inactive, automatically activating, by central computer system, the fast clamp. In some embodiments, activating the fast clamp includes closing the fast clamp. The method may also include querying, by the central computer system, a venous occluder of the heart-lung machine system to determine whether the venous occluder is active or inactive. The method may also include in response to determining that the venous occluder is inactive, automatically activating, by central computer system, the venous occluder. Activating the venous occluder may include adjusting the venous occluder to a pre-configured occlusion setting. The pre-configured occlusion setting may be 50%.

The technology described in this document can provide multiple benefits. For example, the systems and methods described herein can provide semi-autonomous monitoring and control functionality that can be customized by a user (e.g., practitioner, perfusionist, clinician) to meet the user's needs for initiating HLM system components and parameters in desired ranges, quickly identifying any undesired settings, and providing pre-configured parameter setting capability. As a result, the safety and efficacy of HLM operations and perfusion practices can be improved.

In some embodiments, the disclosed systems provide an integrated system that can be used by the user to assess different settings and parameters that are semi-autonomously initiated during the start-up process of a medical procedure. This capability can improve patient safety during the use of the HLM systems described herein. Thus, the disclosed systems and methods provide a single-device solution with integrated, synergistic HLM systems for safe and effective extracorporeal perfusion.

As another example, using the systems and methods described herein, the user can monitor the semi-autonomous start-up procedures of the HLM on a real time basis. Since the start-up parameters are monitored and displayed on the user interface of the HLM in real-time, the user can readily view the status of each of the system components and parameters. As a result, the user can confirm and/or adjust one or more parameters during the start-up and such that the patient experiences no harm.

As yet another example, in some embodiments the disclosed technology can provide pre-configured parameter setting during the start-up of the medical procedure. This is advantageous so that the user does not have to manually calculate or estimate adjustments to the parameter during the start-up. Therefore, because the user can identify desired setting of the parameter before the procedure, the patient's safety and treatment efficacy can be improved.

The disclosed technology can also provide for semi-autonomous control of one or more devices used during medical procedures. The semi-autonomous control can be based on parameters, settings, and parameter adjustments that are configured by the user before the medical procedure. This can assist the user in performing effective perfusion control practices because the user can focus their time on monitoring all the parameters and ensuring the procedure is being correctly performed. During high-stress situations, it can be challenging for the user to monitor all the parameters and make adjustments to one or more devices to establish and maintain the patient's safety. Therefore, having an option to invoke semi-autonomous start-up of one or more devices/parameters based on the user-defined settings prior to the procedure, patient safety and overall perfusion practices can be improved.

The disclosed technology can assist the user in defining parameters and settings for different medical practice areas. Thus, the disclosed technology can provide a high degree of user-customization of controls and monitoring to address a wide range of user and institutional preferences and practices. In other words, the user can define parameters and settings for a first type of medical procedure. Those parameters and settings can be applied to any patient undergoing the first type of medical procedure. The user can then define different parameters and settings for a second type of medical procedure. Those parameters and settings can be applied to any patient undergoing the second type of medical procedure. This provides for a streamlined monitoring and control system that facilitates faster and more efficient preparation before a procedure, and monitoring and control of conditions during the procedure. As a result, patient safety can be improved across the board.

The disclosed technology can provide for optional user-configurable semi-automated functionality. Such user-configurable semi-automated functions can be executed while the user still maintains full manual control capability during a procedure. Thus, the perfusion practice and patient outcomes can be improved.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document describes medical systems that have features for initiating operational settings at the beginning of a medical procedure. For example, this document describes HLM systems that are programmed and integrated with features by which the HLM can perform semi-autonomous start-up procedures.

Figure 1:
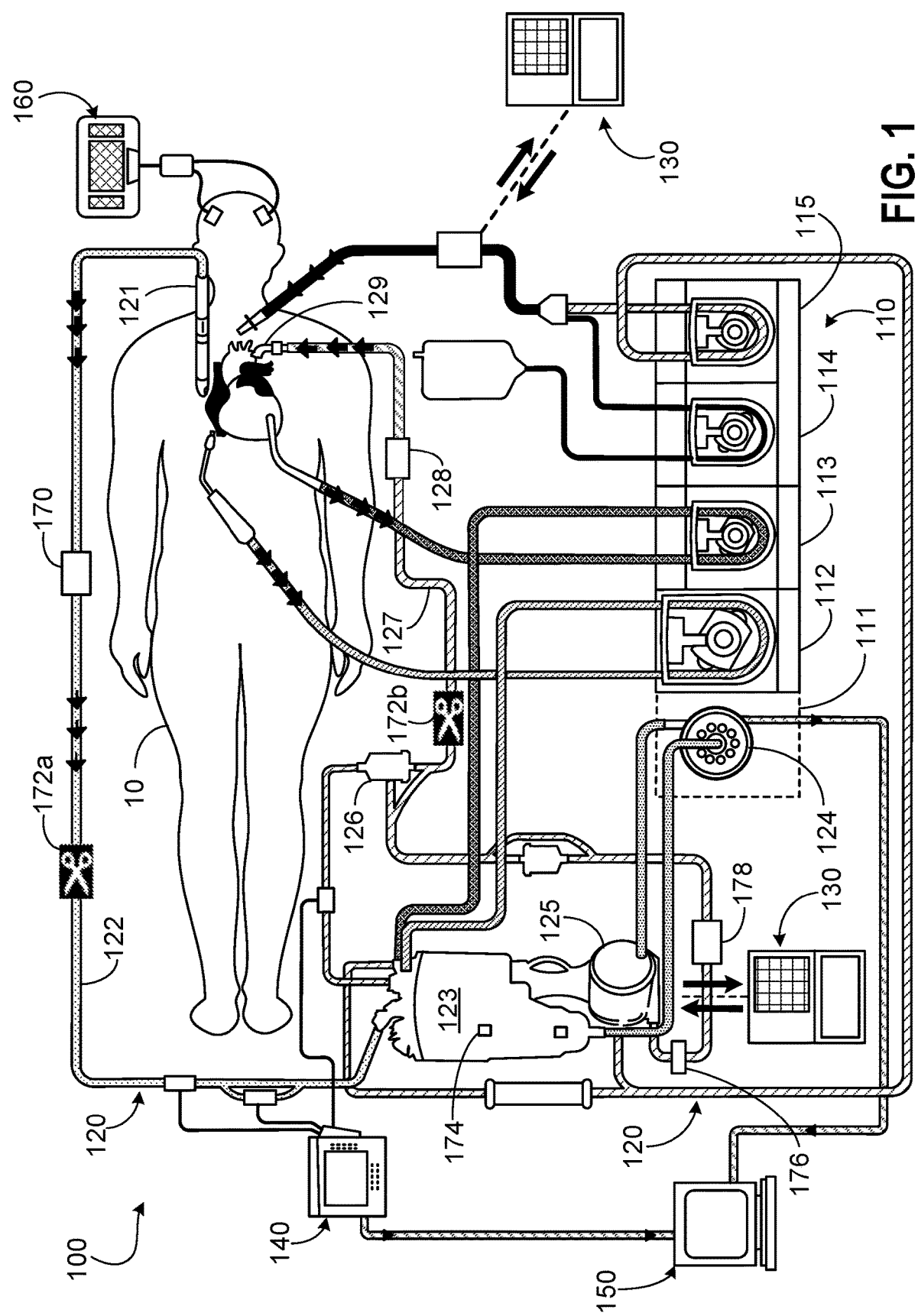
FIG. 1 is a schematic diagram of a patient undergoing open-heart surgery while being supported using a conventional HLM system and extracorporeal circuit.

Now referring to the figures, in FIG. 1, various types of medical procedures can be performed on a patient 10 while the patient 10 is connected to a life-sustaining HLM system 100. In this example, the patient 10 is undergoing open-heart surgery during which the heart 12 and lungs of the patient 10 are temporarily intentionally caused to cease functioning. Because the body of the patient 10 continues to have a metabolic need to receive a supply of circulating oxygenated blood during the medical procedure, however, the HLM system 100 performs such functions. That is, as described further below, the HLM system 100 is connected to the patient 10 and performs the functions of the heart 12 and lungs of the patient 10 so that the patient 10 stays alive and healthy during open-heart surgery.

The HLM system 100 can be used for many different types of medical procedures. For example, the medical procedures for which the HLM system 100 can be used include, but are not limited to, coronary artery bypass grafts, heart valve repairs, heart valve replacements, heart transplants, lung transplants, ablation procedures, repair of septal defects, repair of congenital heart defects, repair of aneurysms, pulmonary endarterectomy, pulmonary thrombectomy, and the like.

The HLM system 100 is typically set up and operated by a specially-trained clinician called a perfusionist. Perfusionists form part of the wider cardiovascular surgical team that includes cardiac surgeons, anesthesiologists, and nurses. During medical procedures using the HLM system 100, the perfusionist is tasked with many responsibilities, not the least of which is ensuring that the patient 10 is kept alive and healthy by operating the HLM system 100 in a manner that maintains blood flow to the patient's tissues, and which regulates levels of oxygen and carbon dioxide in the blood of the patient 10. Other responsibilities of the perfusionist include, but are not limited to, administering blood products, administering anesthetic agents or drugs, measuring selected laboratory values (such as blood cell count), monitoring circulation, monitoring blood gases, surveilling anticoagulation, induction of hypothermia, and hemodilution. The responsibilities of the perfusionist are diverse, dynamic, and critically important to achieving successful outcomes of procedures performed on the patient 10 using the HLM system 100.

In the depicted example, the HLM system 100 includes components and sub-systems such as a HLM 110, an extracorporeal circuit 120, one or more temperature control systems 130, a blood monitoring system 140 (e.g., a CDI® Blood Parameter Monitoring System), a perfusion data management system 150, and a regional oximetry system 160. Some types of procedures that use the HLM system 100 may not require all of the components and sub-systems that are shown. Some types of procedures that use the HLM system 100 may require additional components and/or sub-systems that are not shown.

The extracorporeal circuit 120 is connected to the patient 10, and to the HLM 110. Other systems, such as the temperature control system 130, blood monitoring system 140, and perfusion data management system 150 may also be arranged to interface with the extracorporeal circuit 120. The extracorporeal circuit 120 is connected to the patient 10 at the patient's heart 12. Oxygen-depleted blood (venous blood) from the patient 10 is extracted from the patient 10 at the patient's heart 12 using a venous catheter 121. As described further below, the blood is circulated through the extracorporeal circuit 120 to receive oxygen and remove carbon dioxide. The oxygenated blood is then returned through the extracorporeal circuit 120 to the patient's heart 12 via an aortic cannula 129.

The extracorporeal circuit 120 can include, at least, a venous tube 122 that is coupled to the venous catheter 121, a blood reservoir 123, a centrifugal pump 124, an oxygenator 125, an arterial filter 126, one or more air bubble detectors 128, and an arterial tube 127 that is coupled to the aortic cannula 129. The venous catheter 121 and venous tube 122 are in fluid communication with the venous side of the circulatory system of the patient 10. A venous occluder 170 and a first tube clamp 172a can be located along the venous tube 122. The venous tube 122 is also in fluid communication with an inlet to the reservoir 123. An outlet from the reservoir 123 is connected by tubing to an inlet of the pump 124. The outlet of the pump 124 is connected by tubing to an inlet of the oxygenator 125. The outlet of the oxygenator 125 is connected by tubing to an inlet of the arterial filter 126. An outlet of the arterial filter 126 is connected to the arterial tube 127. One or more pressure transducers can be located along the arterial tube 127 to detect a heart-lung machine (HLM) system line pressure of the blood in the arterial tube 127, which is measured by the HLM 110 and monitored by the perfusionist. In some embodiments, one or more air bubble detectors are located along the extracorporeal circuit 120. The arterial tube 127 is connected to the arterial cannula 129, which is in physical contact with the heart 12 and in fluid communication with the arterial side of the circulatory system of the patient 10.

Briefly, the extracorporeal circuit 120 operates by removing venous, oxygen-depleted blood from the patient 10 via the venous catheter 121, and depositing the venous blood in the reservoir 123 via the venous tube 122. In some cases, gravity is used to cause the blood to flow or drain from the patient 10 to the reservoir 123. In some cases, vacuum is used to assist the blood to flow from the patient 10 to the reservoir 123. At least some amount of blood is intended to be maintained in the reservoir 123 at all times during the surgical procedure. One or more level sensors 174 can be used to detect the level of the blood in the reservoir 123, and to provide feedback used to control the system 100 to maintain the level within a desired range. Otherwise, if the reservoir 123 becomes empty, air could be pumped into the extracorporeal circuit 120, and potentially into the vasculature of the patient 10. Such a result would likely be catastrophic for the patient 10. Accordingly, the perfusionist is tasked with monitoring the level of the blood in the reservoir 123. In addition, the level detectors 174 can be included in conjunction with the reservoir 123 to issue an alarm in response to detection of low-level conditions within the reservoir 123. Moreover, one or more air bubble detectors 128 can be located at various sites along the extracorporeal circuit 120.

Blood from the reservoir 123 is drawn from the reservoir 123 by the pump 124. While the depicted embodiment includes a one-time use centrifugal pump as the pump 124, in some cases a peristaltic pump of the HLM 110 is used instead. The pressure generated by the pump 124 propels the blood through the oxygenator 125. The perfusionist will adjust the pump 124 to operate as desired, while avoiding operational issues such as negative cavitation that could create micro air in the blood of the extracorporeal circuit 120. In the oxygenator 125, the venous blood is enriched with oxygen, and carbon dioxide is removed from the blood. The now oxygen-rich arterial blood exits the oxygenator 125, travels along the arterial tube 127 through multiple components that can include an arterial pressure sensor 176, an arterial fast clamp 178, the arterial filter 126 to remove emboli, and a second tubing clamp 172b. The arterial tube 127 returns oxygenated blood to the patient 10 via the aortic cannula 129.

The extracorporeal circuit 120 can also include tubing and other components for facilitating functions such as, but not limited to, drainage of blood accumulating in the heart of the patient 10, providing surgical suction for maintaining visibility of the surgical field, delivery of cardioplegia solution to the heart 12 of the patient 10 during the procedure, measuring blood parameters, removing air from the blood, hemoconcentration, drug addition, obtaining blood samples, heating and cooling of the blood, and the like.

During a surgical procedure using the HLM system 100, various vital signs of the patient 10 are measured and/or monitored. For example, a patient mean arterial pressure ("MAP") may be measured. The MAP of the patient 10 is a parameter that a perfusionist operating the HLM system 100 will monitor in order to ensure that the HLM system 100 is functioning as desired during the surgical procedure. In some cases, the MAP reading is displayed on a screen of an anesthesia system, and/or displayed on the operating room screen. If the MAP of the patient 10 is outside of a desired range, the perfusionist may make adjustments to the HLM system 100 to improve the MAP of the patient 10.

The HLM system 100 also includes the HLM 110. The HLM 110 is a complex system that includes multiple pumps, monitors, controls, user interfaces, alarms, safety devices, and the like, that are all monitored and operated/adjusted by the perfusionist during a surgical procedure. For example, the depicted HLM 110 includes an arterial pump 111 (which can be a drive system for a disposable centrifugal pump 124 as shown, or a peristaltic pump), a suction pump 112, a vent/drainage pump 113, a cardioplegia solution pump 114, and a cardioplegia delivery pump 115. The HLM 110 can also include, or be interfaced with, devices such as a tubing occluder, electronic gas blender system, hemoconcentrator, and the like. The parameters of the HLM 110, such as the rotational speed and other parameters of each of the pumps, are set and adjusted by the perfusionist. For example, the speed of the arterial pump 111 is adjusted to maintain a desirable level of blood in the reservoir 123, and to provide a requisite level of blood circulation within the patient 10.

The HLM system 100 also includes one or more temperature control systems 130. In a first aspect, the temperature control system(s) 130 is/are used to heat and cool the patient's blood in the oxygenator 125 via a heat exchanger. Additionally, the temperature control system(s) 130 is/are used to heat and cool the cardioplegia solution being delivered to the heart 12 of the patient 10. In general, the temperature control system(s) 130 is/are used in cooling modes during the procedure (to reduce metabolic demands), and subsequently used to warm the blood and/or cardioplegia solution when the surgical procedure is nearing its end. The perfusionist is tasked with setting up and monitoring/adjusting the temperature control system(s) 130 as needed during the surgical procedure.

The HLM system 100, as depicted, also includes the blood monitoring system 140. The blood monitoring system 140 is used to monitor the extracorporeal blood of the patient 10 during the surgical procedure. Parameters being monitored can include, but are not limited to, pH, $pCO_2$, $pO_2$, K+, temperature, $SO_2$, hematocrit, hemoglobin, base excess, bicarbonate, oxygen consumption and oxygen delivery. The perfusionist is tasked with setting up and monitoring the blood monitoring system 140 during the surgical procedure. In some cases, the perfusionist will need to adjust other components or subsystems of the HLM system 100 in response to readings from the blood monitoring system 140.

The HLM system 100, as depicted, also includes the perfusion data management system 150 and the regional oximetry system 160. These systems can also be used by the perfusionist to monitor the status of the patient 10 and/or the status of the HLM system 100 during surgical procedures.

Various systems, sub-systems, and components of the HLM system 100 have been described above. In some cases, the HLM system 100 for a particular patient 10 will be fully configured with all of the systems, sub-systems, and components described above. In other cases, one or more of the above-described systems, sub-systems, and components of the HLM system 100 may not be put in use for other patients 10. Such variations in terms of what systems, sub-systems, and components are used for a particular procedure can be due to many different factors and combinations of factors, such as the type of patient (e.g., adult, pediatric, body mass, comorbidities, etc.), the healthcare institution's standard procedures, a surgeon's preferences, a perfusionist's preferences, equipment availability, and so on. Accordingly, the perfusionist must be prepared to set-up and start-up a wide variety of different configurations of the HLM system 100. This can be very challenging and stressful for the perfusionist.

From the above description, it can be observed and understood that the perfusionist is tasked with a vast amount of very important responsibilities to set-up and start-up a surgical procedure using the conventional HLM system 100. Some of the tasks pertain to the HLM 110, others pertain to the extracorporeal circuit 120, and still others pertain to additional sub-systems of the HLM system 100. Accordingly, this disclosure describes systems and techniques that can assist the perfusionist to perform successfully the set-up and start-up of the HLM system 100.

Figure 2A:
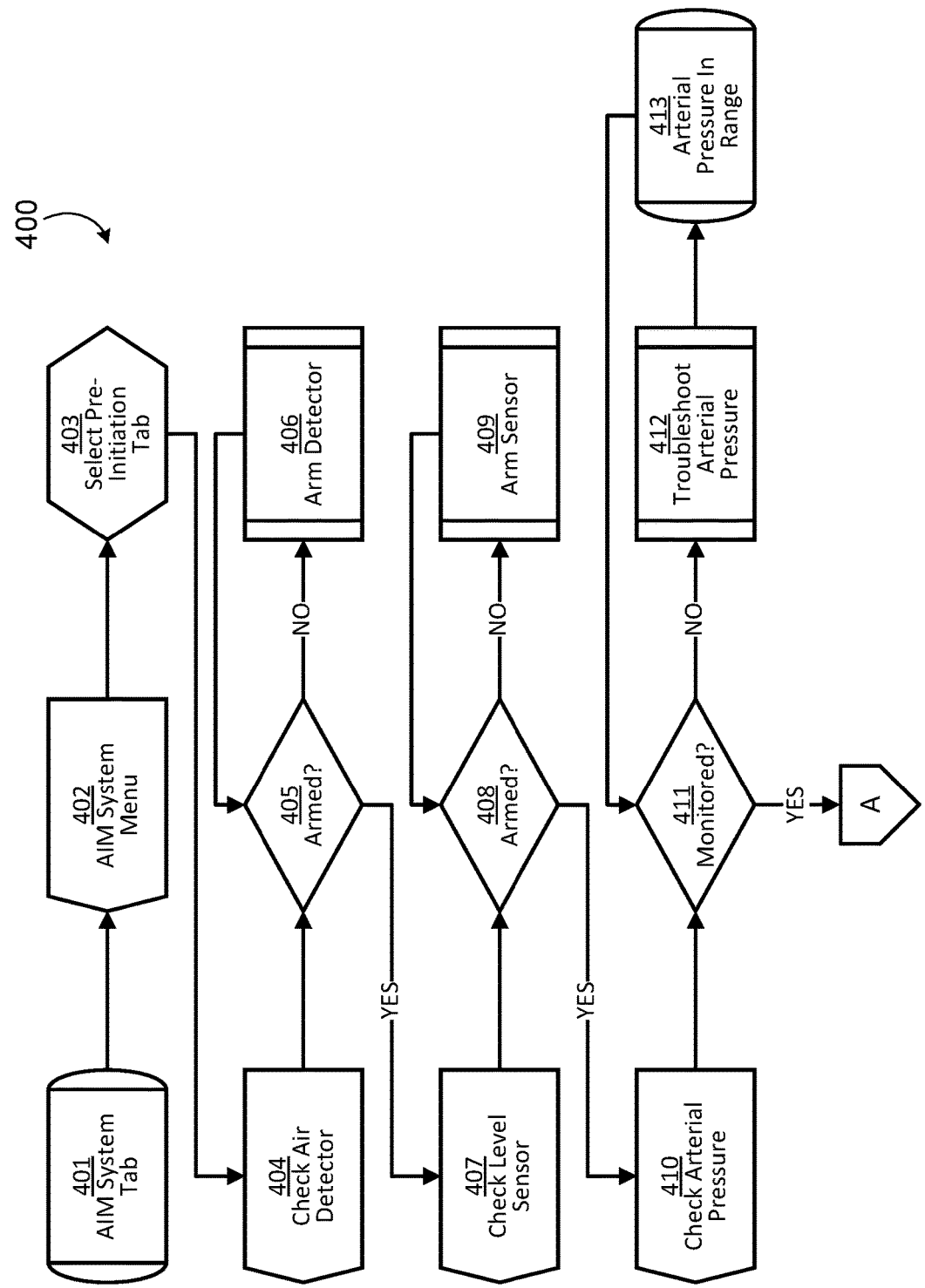
FIGS. 2a and 2b are a flowchart of an example process for a semi-autonomous initiation mode of the HLM system and extracorporeal circuit of FIG. 1.
Figure 2B:
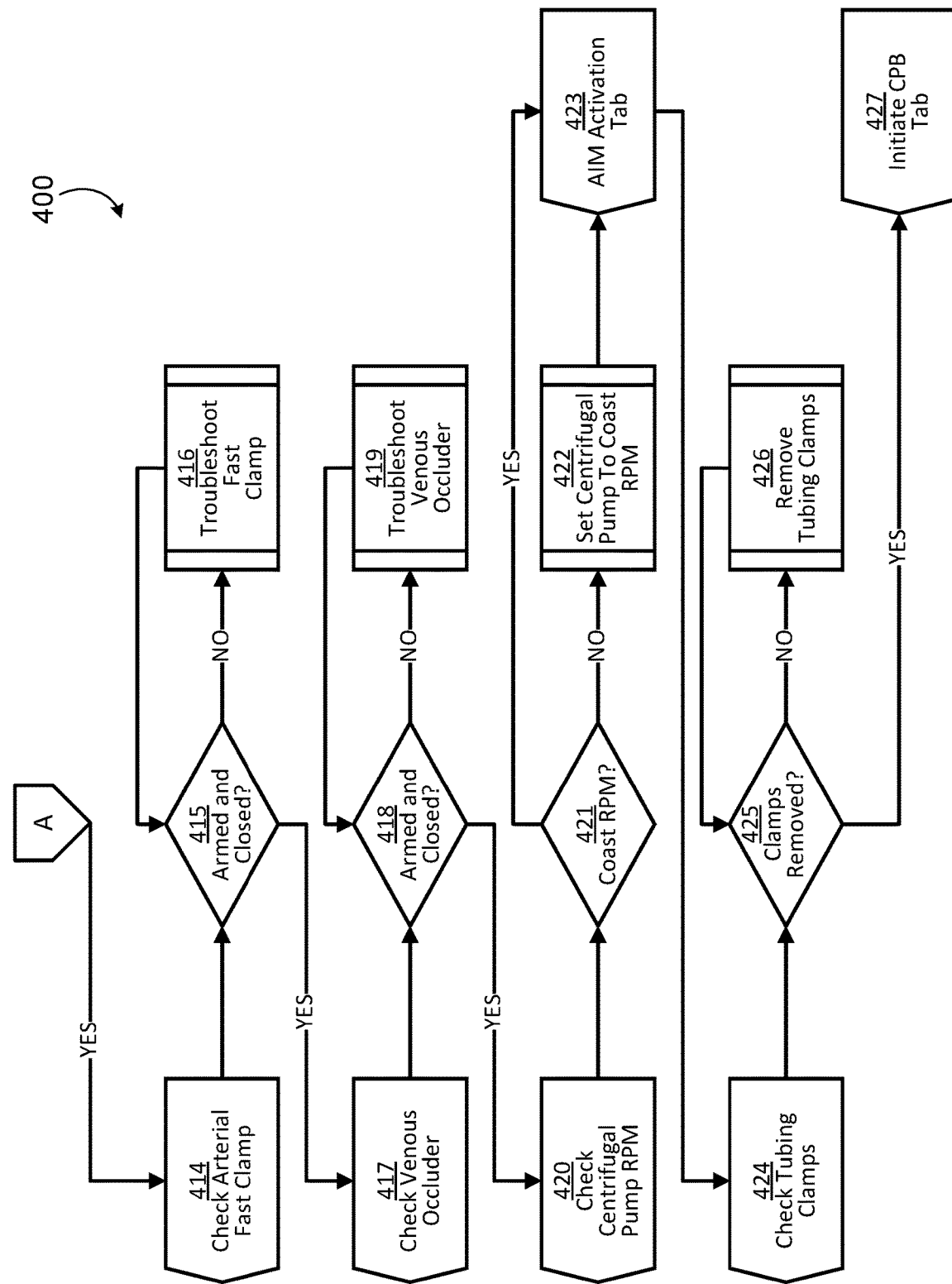

FIGS. 2a and 2b are a flowchart of a semi-autonomous initiation mode process 400 ("AIM process 400") for starting-up the HLM system 100. The AIM process 400 describes the operations of a semi-autonomous initiation mode system ("AIM system") for the start-up of the HLM system 100 and other medical equipment systems. In some embodiments, the AIM process 400 would be performed after set-up and priming, and while awaiting surgeon direction to initiate cardiopulmonary bypass.

Some of the purposes and benefits of the AIM system and the AIM process 400 include mitigation of the risks related to perfusionist oversights such as not activating all of the safety alarms, not turning on the oxygen supply to the oxygenator 125, not fully closing the venous occluder 170 or fast clamp 178, not activating the level sensors 174, not activating the air bubble detector ("ABD"), and so on. In addition, the AIM system and the AIM process 400 can beneficially reduce the number of tasks that the perfusionist must otherwise perform to set-up, activate and test the systems, sub-systems, and components of the HLM system 100.

It should be understood that some steps of the AIM process 400 may be omitted in some cases. The omission of certain steps can be attributable to, or based on, the particular configuration of the HLM system 100 being used, the perfusionist's preferences, and other factors. Moreover, the AIM system can be configured to perform, or not perform, any of the steps of the AIM process 400. Accordingly, each of the steps of the AIM process 400 should be considered to be optional steps.

The AIM system can be integrated with the HLM system 100. In some embodiments, the AIM process 400 can be a part of, or can be executed by, the central computer of the HLM 110.

In step 401 of the AIM process 400, the AIM system tab on the user interface of the HLM 110 is accessed by a user (e.g., perfusionist). In response, the user interface of the HLM 110 will display the AIM system menu in step 402. In some embodiments, this action provides the perfusionist with an opportunity to review and/or adjust the systems, sub-systems, and components of the HLM system 100 that will be semi-autonomously checked and/or activated during the performance of the AIM process 400.

From the AIM system menu, the perfusionist can start the semi-autonomous checking and activating process by selecting an element on the user interface such as the pre-initiation tab 403. In response, the user interface of the HLM 110 will display an overview of the systems, sub-systems, and components of the HLM system 100 that will be semi-autonomously checked. In addition, the semi-autonomous checking and activating process will begin. That is, the AIM system will start sequentially querying and sending activation signals to systems, sub-systems, and components of the HLM system 100, as described in the following steps of the AIM process 400. As each of the following steps is performed, indications of the statuses of the systems, sub-systems, and components of the HLM system 100 can be provided on the user interface display. For example, in some embodiments the AIM system display screen on the user interface can have a tabular listing of the parameters to be checked. Indications, such as a green light beside each parameter, can be provided when the parameter has been successfully and properly activated.

In steps 404 and 405 of the AIM process 400, the AIM system queries the air detector (e.g., air bubble detector as described above) to determine whether the air detector is activated (or "armed"). If the air detector is armed, then the next action of the AIM process 400 is step 407. However, if the air detector is not armed then the next action of the AIM process 400 is step 406. In step 406 of the AIM process 400, the AIM system arms the air detector. Then, the AIM system once again performs step 405 in which the AIM system checks to confirm that the air detector is armed. When the AIM system has confirmed that the air detector is armed, the user interface display provides an indication, and then the AIM system proceeds to step 407. Hence, as can be envisioned from this first example (which is representative of the other steps of the AIM process 400), it can be said that the AIM system performs the AIM process 400 semi-autonomously because the AIM system will arm the air detector in step 406 when the AIM system finds (in step 405) that the air detector is not armed.

In steps 407 and 408 of the AIM process 400, the AIM system checks/queries the reservoir level detector(s) to determine whether the reservoir level detector(s) is/are armed. If the AIM system determines, in step 408, that the reservoir level detector(s) is/are not armed, then the AIM system arms the reservoir level detector(s) in step 409. It should be understood that at this time the reservoir may not yet contain fluid in the area of the reservoir level detector(s). Accordingly, even though the reservoir level detector(s) is/are armed, the AIM system can initially suppress alarms from the reservoir level detector(s) that would otherwise be generated by the lack of fluid (e.g., blood) in the area of the reservoir level detector(s). However, when fluid is initially detected in the area of the reservoir level detector(s), in response the AIM system can then discontinue the suppression of the alarms. When the AIM system confirms that the reservoir level detector(s) is/are armed, the user interface display provides a corresponding indication and the AIM process 400 proceeds to step 410.

In steps 410 and 411 of the AIM process 400, the AIM system checks/queries the arterial pressure sensor sub-system (e.g., the arterial pressure sensor 176 of FIG. 1). In particular, in some embodiments the AIM system can check and verify that a low pressure limit and a high pressure limit have been set, and that an arterial pressure sensor is communicative to the AIM system.

In step 412 of the AIM process 400, the AIM system troubleshoots the arterial pressure sensor sub-system. For example, this can include troubleshooting a non-displayed line pressure by checking points to determine whether the transducer is zeroed correctly, whether the stopcock is turned inline in the correct position to read the line pressure, whether the pressure cable is secured correctly to the transducer, and so on.

In step 413 of the AIM process 400, the AIM system determines whether the arterial pressure is in range. At this step, the surgeon has already cannulated the aorta and connected the arterial tubing of the primary circuitry to the cannula and removed the clamp at that connection. Once the connection is made, the perfusionist monitors the line pressure that is being transduced from the aorta. This range typically may be from 100 to 200 mmHg, depending on the systemic pressure of the patient and the pressure in the aorta. The perfusionist then places a clamp on the arterial line near him/her to safely secure the patient until it is time to initiate bypass.

When the AIM system confirms that the arterial pressure sensor sub-system is properly operating, the user interface display provides a corresponding indication and the AIM process 400 proceeds to step 414.

In steps 414 and 415 of the AIM process 400, the AIM system checks/queries the fast clamp sub-system (e.g., the arterial fast clamp 178 of FIG. 1) to determine whether the fast clamp is employed and, if so, whether the fast clamp is armed and closed. If the fast clamp is employed, but not armed and/or closed, the AIM system can semi-autonomously arm and/or close the fast clamp in step 416. When the AIM system confirms that the fast clamp is properly operating (and is closed), the user interface display provides a corresponding indication and the AIM process 400 proceeds to step 417.

In steps 417 and 418 of the AIM process 400, the AIM system checks/queries the venous occluder sub-system (e.g., the venous occluder 170 of FIG. 1) to determine whether the occluder is employed and, if so, whether the occluder is armed and closed. If the occluder is employed, but not armed and/or closed, the AIM system can semi-autonomously arm and/or close the occluder in step 419. When the AIM system confirms that the occluder is properly operating (and is closed), the user interface display provides a corresponding indication and the AIM process 400 proceeds to step 420.

In steps 420 and 421 of the AIM process 400, the AIM system checks/queries the centrifugal pump (if a centrifugal pump is employed). For example, the AIM system checks that the RPM of the centrifugal pump is set at a configurable coast speed set-point. If not, the AIM system can semi-autonomously increase or decrease the RPM of the centrifugal pump to operate at the configured coast speed (RPM). When the AIM system confirms that the centrifugal pump is properly operating (and its RPM is at the established coast speed), the user interface display provides a corresponding indication in step 423, and the AIM process 400 proceeds to step 424.

In steps 424 and 425 of the AIM process 400, the AIM system checks/queries to determine whether the tubing clamps (e.g., the clamps 172a and 172b of FIG. 1) are clamping closed the extracorporeal circuit, or whether the tubing clamps are not clamping the extracorporeal circuit. In some embodiments, this is performed by providing a message on the user interface and asking the perfusionist to confirm that the clamps are removed by inputting a response into the user interface. In some cases, if the AIM system determines that one or more of the clamps are closing the extracorporeal circuit, a message can be displayed on the user interface to prompt the perfusionist to remover the one or more clamps. When the AIM system determines that the clamps are not closing the extracorporeal circuit, then the AIM process 400 proceeds to step 427.

At step 427 of the AIM process 400, the AIM system initiates CPB. This step can include one or more of the following actions that are performed by the AIM system and/or by the central computer system of the HLM in an autonomous or a semi-autonomous manner. The pump time clock can be started. The gas sweep can be adjusted to a pre-configured setting (e.g., 1 L/min for adults for a semi-autonomous target flow). The FiO2 can be adjusted to a pre-configured setting (e.g., 100 percent for adults for a semi-autonomous target). The arterial fast clamp (if employed) can be opened. The arterial blood flow can be gradually ramped up over a period of time (configurable, for example 20 seconds) to a pre-configured target value (e.g., 1 L/min for adults). The AIM system would be limited by a configurable safe upper flow limit to keep the semi-autonomous operations in control. That is, it would still be incumbent on the Perfusionist to adjust the blood flow to a full flow target value and to control the venous return. The venous occluder (if employed) can be opened to a pre-configured setting (e.g., 50 percent open for a semi-autonomous target flow).

In some embodiments, the AIM system and/or by the central computer system of the HLM would autonomously or semi-autonomously monitor the perfusion system in terms of venous reservoir level, arterial line pressure, and air detection, with appropriate responses for all, as the AIM system reaches its target flow value.

Intervention by the perfusionist on the arterial pump blood flow (e.g., speed adjustment knob or cursor) during the AIM system-controlled start up would immediately disengage the AIM system, returning full control to the perfusionist. Once the AIM system and/or the central computer system of the HLM reaches its pre-configured semi-autonomous target arterial flow, the perfusionist assumes manual control of CPB and increases arterial pump flow to full flow index and adjusts control of venous return. The AIM system automatically disengages with the adjustment of the arterial pump blood flow.

Figure 3:
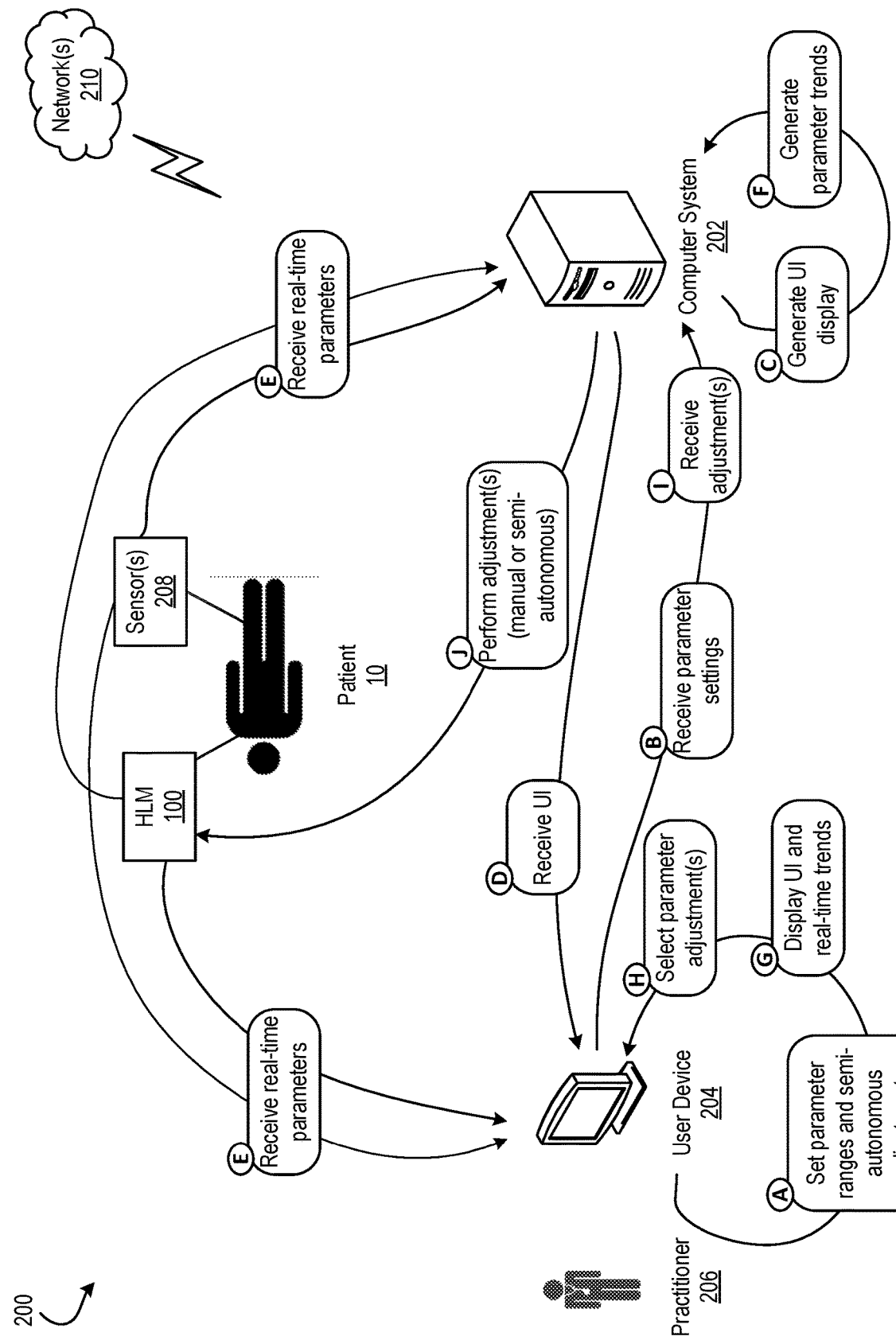
FIG. 3 is a process flow diagram of an example procedure using the HLM system and extracorporeal circuit of FIG. 1.

FIG. 3 is a schematic diagram of an example monitoring and control system used during a medical procedure 200. The procedure 200 can include the patient 10 and a practitioner 206. The practitioner 206 can be a perfusionist or other professional who performs the procedure 200 and/or portions of the procedure 200. The patient 10 can be hooked up or in communication with the HLM (e.g., HLM system 100), as depicted and described throughout this disclosure. Sensor(s) 208 can also be attached to the patient 10 or the extracorporeal circuit. The sensor(s) 208 can further be in communication with the HLM system 100 and/or any other devices used during the procedure 200. The sensor(s) 208 can capture real-time conditions of the patient 10, the HLM system 100, and parameters that are being monitored during the procedure 200.

The practitioner 206 can use a user device 204 (user interface) to monitor conditions or parameters of the patient 10, the HLM system 100, and other devices used during the procedure 200. In some embodiments, the user device 204 is part of the HLM system 100, or physically attached thereto. In some embodiments, the user device 204 can be separate from the HLM system 100. In some embodiments, the user device 204 can be a mobile computing device, such as a smartphone or tablet. The user device 204 can also be a computer or laptop. The user device 204 can have a user interface (e.g., touchscreen, monitor, etc.) configured to display monitored conditions and parameters in real-time. The user device 204 can also have one or more input devices configured to receive adjustments from the practitioner 206. The practitioner 206 can make adjustments to any one of the conditions and parameters by providing input to the user device 204.

The user device 204 can be in communication with a computer system 202 (e.g., monitoring and control system). In some embodiments, the computer system 202 is part of the HLM system 100. In some embodiments, the user device 204 is part of the computer system 202. Moreover, the computer system 202 can include one or more input devices and/or displays. The AIM system can be installed to run on the computer system 202.

The computer system 202 can be configured to provide the user device 204 with a user interface that displays monitored conditions and parameters. In some implementations, the computer system 202 and the user device 204 can be the same system. In other implementations, the computer system 202 and the user device 204 can be remote from each other. The computer system 202 can also facilitate one or more adjustments made or suggested by the practitioner 206 during the procedure 200. Therefore, the computer system 202 can also be in communication with the HLM system 100, the sensor(s) 208, and any other devices that are used during the procedure 200. Communication between one or more components (e.g., the user device 204, the FILM 110, the sensor(s) 208, and the computer system 202) can be wireless and/or wired via network(s) 210.

Still referring to FIG. 2, before the procedure 200 begins, the practitioner 206 can set parameter ranges and semi-autonomous adjustments at the user device 204 (A). The user device 204 can provide a display to the practitioner 206, prompting the practitioner 206 to set values for each of the parameters that will be monitored during the procedure 200. The practitioner 206 can also be prompted to input desired adjustments to the parameters that the practitioner 206 may want implemented during the procedure 200 if the parameters stray from the practitioner-defined parameter ranges. In other words, before the procedure 200, the practitioner 206 can indicate what actions (e.g., pre-defined adjustments) can be taken should any of the parameters exceed or fall below ideal ranges that the practitioner 206 also defines before the procedure 200. Then, during the procedure 200, if any of the parameters do in fact stray outside of the practitioner-defined ranges, the practitioner 206 can select and perform one of the pre-defined adjustments. Such adjustments can be performed manually by the practitioner 206. Such adjustments can also be performed semi-autonomously by the computer system 202.

The practitioner 206 can set parameter ranges and semi-autonomous adjustments that apply generally to all similar procedures or a specific practice area. Therefore, regardless of which patient undergoes the procedure 200, the same parameter ranges and semi-autonomous adjustments can be applied to the procedure 200. This can be beneficial for the practitioner 206 to perform all procedures the same way, which can improve patient safety and overall procedure outcomes. Moreover, using the same parameter ranges and semi-autonomous adjustments in a specific practice area can be advantageous for the computer system 202 to more accurately predict and/or generate parameter trend analysis. In other examples, the practitioner 206 can set parameter ranges and semi-autonomous adjustments per procedure per patient. In other words, first and second patients can undergo the same procedure. However, the practitioner 206 can set different parameter ranges and adjustments for each of the patients. This can be beneficial where the patients have different health conditions or sensitivities.

Next, the computer system 202 can receive the parameter settings from the user device 204 (B). These parameter settings can be one or more of the practitioner-defined parameter ranges and/or semi-autonomous parameter adjustments.

Based on the received parameter settings, the computer system 202 can generate one or more user interface displays (C). For example, the computer system 202 can generate interactive/selective options on a user interface, wherein each of the selective options correlates to a semi-autonomous adjustment that the practitioner 206 defined at the user device 204. In other words, if the practitioner 206 defined an adjustment to increase blood flow through the extracorporeal circuit in the HLM system 100, the computer system 202 can generate a button that, when clicked on by the practitioner 206 during the procedure 200, can automatically cause the blood flow to be increased through the circuit. As another example, the computer system 202 can also generate one or more graphs or other depictions for each of the parameters that the practitioner 206 defined at the user device 204.

The generated user interface display can be received at the user device 204 (D). In other words, the user interface can be displayed on the user device 204 during the procedure 200. The display can be updated during the procedure 200 to reflect real-time changes in parameters, parameter trends, and/or conditions of the patient 10. The display, as depicted and described throughout this disclosure, can provide information for each of the monitored or defined parameters on a single user interface. As a result, in some embodiments the practitioner 206 can monitor all parameters during the procedure 200 concurrently. In other implementations, the practitioner 206 can switch between multiple different user interface displays/screens. Each of the user interface displays/screens can be related to a particular parameter. Each of the user interfaces can be related to a subset of all of the practitioner-defined parameters.

In some cases, consolidating the parameters into a singular user interface display can be advantageous. This is because the practitioner 206 can more easily and continuously monitor all parameters during the procedure 200. With real-time updates, the practitioner 206 can also more quickly and accurately respond to any undesired changes in the parameters.

The user device 204 can receive real-time parameter information from the HLM system 100 and/or the sensor(s) 208 during the procedure (E). The computer system 202 can also receive real-time parameter information from the HLM system 100 and/or the sensor(s) 208 (E). Based on the real-time parameter information, the computer system 202 can generate parameter trends (F). For example, the computer system 202 can generate graphs depicting a trend analysis of each of the monitored parameters. The graphs can indicate past, current, and projected trends of the monitored parameters. The graphs can also indicate past, current, and projected trends of the monitored parameters relative to the practitioner-defined parameter ranges.

The generated parameter trends can be provided from the computer system 202 to the user device 204. Therefore, the parameter trends can be displayed at the user interface (G). Thus, the user interface can be dynamically updated as real-time parameter information is received (E) and parameter trends are generated (F). In some implementations, the user device 204 can determine and generate the parameter trends. The user device 204 can also display the real-time parameter information that is received from the HLM system 100 and/or the sensor(s) 208 (G). For example, the user device 204 can update the user interface with parameter values that are sensed in real-time by the sensor(s) 208. That user interface can also be updated to reflect the parameter trends generated by the computer system 202 (F). Thus, the user interface can display both the present or current parameter values as well as the projected parameter trends.

As all this information is displayed to the practitioner 206 at the user device 204, the practitioner can choose whether or not to make any adjustments to affect the monitored parameters. For example, if one of the parameters is projected to trend out of the practitioner-defined range for that parameter, then the practitioner 206 can select one of the practitioner 206's pre-defined parameter adjustments from the user interface (H). As mentioned, the pre-defined parameter adjustments can be displayed in the user interface as a selectable option, such as a button.

When the practitioner 206 selects one or more of the pre-defined parameter adjustments, the computer system 202 can receive the adjustment from the user device 204 (I). In some implementations, the practitioner 206 can select more than one pre-defined parameter adjustment. Selections by the practitioner 206 can be communicated and performed simultaneously by the computer system 202.

The parameter adjustment(s) can then be performed (J). In some embodiments, the parameter adjustment can be semi-autonomously performed by the computer system 202. In other words, the practitioner 206 defined the adjustment before the procedure 200 began. When the practitioner 206 selected the pre-defined parameter adjustment during the procedure 200, the computer system 202 received instructions to execute the adjustment. Therefore, the practitioner 206 maintains control of what type of adjustments occur during the procedure 200. In some embodiments, the computer system 202 does not predict or suggest to the practitioner 206 what adjustment(s) to make. Alternatively, in some embodiments the computer system 202 does suggest to the practitioner 206 what adjustment(s) to make.

In other examples, the adjustment(s) can be performed manually by the practitioner 206. The practitioner 206 can also override a semi-autonomous adjustment by selectively controlling one or more buttons or other physical components of the user device 204, the HLM system 100, and/or any other device that is used during the procedure 200. For example, the practitioner 206 may have established a pre-defined parameter adjustment before the procedure 200 that required increasing pressure through a particular portion of the extracorporeal circuit by a first value. During the procedure 200, the practitioner 206 may still want to perform that adjustment but increase pressure through the particular portion of the extracorporeal circuit by a second value instead of the first value. The second value can be greater or less than the first value. Therefore, the practitioner 206 can manually take control and operate one or more physical buttons to adjust the pressure by the second value. This can be a manual or semi-manual performance of a pre-defined adjustment.

The user device 204 and the computer system 202 can continue to receive real-time parameter information during the procedure 200, after such one or more adjustments have been made. As a result, the practitioner 206 can continuously monitor the parameters and make any necessary adjustments throughout the procedure 200.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A heart-lung machine system comprising:
an arterial pump;
a reservoir level detector system comprising two reservoir level detectors and by which a level of fluid in a reservoir is maintainable between the two reservoir level detectors;
a user interface; and
a central computer system configured to:
query the reservoir level detector system to determine whether the reservoir level detector system is active or inactive;
in response to determining that the reservoir level detector system is inactive, automatically activate the reservoir level detector system;
in response to the automatic activation of the reservoir level detector system:
(i) automatically generate an indication for display on the user interface that the reservoir level detector system is active, and
(ii) automatically prevent alarms related to detection of a lack of fluid by the reservoir level detector system from being generated; and
after the automatic prevention of the alarms related to the detection of the lack of fluid by the reservoir level detector system, discontinue the automatic prevention of the alarms in response to a first detection of fluid by the reservoir level detector system.

2. The heart-lung machine system of claim 1, further comprising an air detector, and wherein the central computer system is further configured to:
query the air detector to determine whether the air detector is active or inactive; and
in response to determining that the air detector is inactive, automatically activate the air detector.

3. The heart-lung machine system of claim 1, further comprising a fast clamp, and wherein the central computer system is further configured to:
query the fast clamp to determine whether the fast clamp is active or inactive; and
in response to determining that the fast clamp is inactive, automatically activate the fast clamp by closing the fast clamp.

4. The heart-lung machine system of claim 1, further comprising a venous occluder, and wherein the central computer system is further configured to:
query the venous occluder to determine whether the venous occluder is active or inactive; and
in response to determining that the venous occluder is inactive, automatically activate the venous occluder by adjusting the venous occluder to a pre-configured occlusion setting.

5. The heart-lung machine system of claim 1, wherein the arterial pump is a centrifugal pump, and wherein the central computer system is further configured to:
query the centrifugal pump to determine whether the centrifugal pump is active or inactive; and
in response to determining that the centrifugal pump is inactive, automatically activate the centrifugal pump by adjusting the centrifugal pump to a pre-configured RPM setting.

6. The heart-lung machine system of claim 5, wherein the central computer system is configured to stop adjusting the centrifugal pump to the pre-configured RPM setting in response to a manual input to the heart-lung machine system that effects the pre-configured RPM setting of the centrifugal pump.

7. A method of operating a heart-lung machine system, the method comprising:
querying, by a central computer system of the heart-lung machine system, a reservoir level detector system of the heart-lung machine system to determine whether the reservoir level detector system is active or inactive, wherein the reservoir level detector system comprises two reservoir level detectors;
in response to determining that the reservoir level detector system is inactive, automatically activating, by the central computer system of the heart-lung machine system, the reservoir level detector system;
in response to the automatic activation of the reservoir level detector system, automatically preventing, by the central computer system of the heart-lung machine system, alarms related to detection of a lack of fluid by the reservoir level detector system from being generated; and
discontinuing, by the central computer system of the heart-lung machine system, the automatic prevention of the alarms in response to a first detection of fluid by the reservoir level detector system after the automatic prevention of the alarms.

8. The method of claim 7, further comprising:
querying, by the central computer system, a centrifugal pump of the heart-lung machine system to determine whether the centrifugal pump is active or inactive; and
in response to determining that the centrifugal pump is inactive, automatically activating the centrifugal pump by the central computer system.

9. The method of claim 8, wherein automatically activating the centrifugal pump includes adjusting, by the central computer system, the centrifugal pump to a pre-configured RPM setting.

10. The method of claim 9, further comprising stopping, by the central computer system, adjusting the centrifugal pump to the pre-configured RPM setting in response to a manual input to the heart-lung machine system that effects the pre-configured RPM setting of the centrifugal pump.

11. The method of claim 7, further comprising:
querying, by the central computer system, an air detector of the heart-lung machine system to determine whether the air detector is active or inactive; and
in response to determining that the air detector is inactive, automatically activating, by the central computer system, the air detector.

12. The method of claim 7, further comprising:
querying, by the central computer system, a fast clamp of the heart-lung machine system to determine whether the fast clamp is active or inactive; and
in response to determining that the fast clamp is inactive, automatically activating, by the central computer system, the fast clamp.

13. The method of claim 12, wherein the activating the fast clamp includes closing the fast clamp.

14. The method of claim 7, further comprising:
querying, by the central computer system, a venous occluder of the heart-lung machine system to determine whether the venous occluder is active or inactive; and
in response to determining that the venous occluder is inactive, automatically activating, by the central computer system, the venous occluder.

15. The method of claim 14, wherein activating the venous occluder comprises adjusting the venous occluder to a pre-configured occlusion setting.

16. The method of claim 15, wherein the pre-configured occlusion setting is 50%.

\* \* \* \* \*